(12) United States Patent
Gibson et al.

(10) Patent No.: US 8,545,895 B2
(45) Date of Patent: Oct. 1, 2013

(54) SILICATE-SUBSTITUTED HYDROXYAPATITE

(75) Inventors: Iain Ronald Gibson, Aberdeen (GB); Janet Mabel Scott Skakle, Aberdeen (GB)

(73) Assignee: The University Court of the University of Aberdeen, Aberdeenshire (GB)

( * ) Notice: Subject to any disclaimer, the term of this patent is extended or adjusted under 35 U.S.C. 154(b) by 239 days.

(21) Appl. No.: 12/652,110

(22) Filed: Jan. 5, 2010

(65) Prior Publication Data

US 2010/0173009 A1    Jul. 8, 2010

(30) Foreign Application Priority Data

Jan. 8, 2009   (GB) .................................. 0900269.2

(51) Int. Cl.
| | |
|---|---|
| *A61K 33/42* | (2006.01) |
| *A61K 6/00* | (2006.01) |
| *C09D 1/00* | (2006.01) |
| *C01B 25/32* | (2006.01) |
| *A61P 19/08* | (2006.01) |

(52) U.S. Cl.
USPC .......................... 424/602; 106/286.6; 423/308

(58) Field of Classification Search
None
See application file for complete search history.

(56) References Cited

U.S. PATENT DOCUMENTS

| | | | |
|---|---|---|---|
| 4,693,986 | A | 9/1987 | Vit et al. |
| 4,731,394 | A | 3/1988 | Vogel et al. |
| 5,989,030 | A | 11/1999 | Suga |
| 6,312,468 | B1 * | 11/2001 | Best et al. ................. 623/16.11 |
| 2002/0136696 | A1 | 9/2002 | Lee et al. |
| 2002/0173850 | A1 | 11/2002 | Brodke et al. |
| 2004/0010313 | A1 | 1/2004 | Aston et al. |
| 2004/0078087 | A1 | 4/2004 | Kim et al. |
| 2004/0146752 | A1 | 7/2004 | Axen et al. |
| 2004/0191292 | A1 | 9/2004 | Chou |
| 2004/0202985 | A1 | 10/2004 | Karmaker et al. |
| 2004/0230309 | A1 | 11/2004 | DiMauro et al. |
| 2005/0049715 | A1 | 3/2005 | Ito et al. |
| 2005/0069573 | A1 | 3/2005 | Cohn et al. |
| 2005/0069629 | A1 | 3/2005 | Becker et al. |
| 2005/0074877 | A1 | 4/2005 | Mao |
| 2005/0100578 | A1 | 5/2005 | Schmid et al. |
| 2005/0197422 | A1 | 9/2005 | Mayadunne et al. |
| 2005/0241535 | A1 | 11/2005 | Bohner |
| 2005/0244449 | A1 | 11/2005 | Sayer et al. |
| 2005/0249773 | A1 | 11/2005 | Maspero et al. |
| 2008/0274185 | A1 | 11/2008 | Mao |
| 2009/0068272 | A1 | 3/2009 | Bandyopadhyay et al. |
| 2009/0162414 | A1 | 6/2009 | Hing et al. |
| 2009/0276056 | A1 | 11/2009 | Bose et al. |

FOREIGN PATENT DOCUMENTS

| | | |
|---|---|---|
| GB | 395713 | 7/1933 |
| GB | 2395713 | 6/2004 |
| JP | 2002 137914 | 5/2002 |
| WO | WO 98/44964 | 10/1998 |
| WO | WO 99/38542 | 8/1999 |
| WO | WO 2006/118554 | 11/2006 |
| WO | WO-2009/087390 | 7/2009 |
| WO | WO 2009/095703 | 8/2009 |

OTHER PUBLICATIONS

Guth et al., Key Eng. Mater., 2006, 309-311, pp. 117-120.
C.P.A.T. Klein et al, J. Biomed. Mater. Res., 1983, 17, 769.
I.D. Xynos et al, Calc. Tiss. Int., 2000, 67, 321-329.
Palard et al, Journal of Solid State Chemistry, 181 (2008) 1950-1960.
I.R. Gibson et al, J. Biomed. Mater. Res. 44(1999)422-428.
Reid, J W et al, "Synthesis and characterization of single-phase silicon-substituted alpha-tricalcium phosphate", Biomaterials, vol. 27, No. 15, pp. 2916-2925, May 1, 2006.
International Search Report and Written Opinion of the International Searching Authority issued Apr. 19, 2010 for Int'l Application No. PCT/GB2009/002954, European Patent Office, Rijswijk, Netherlands.

* cited by examiner

*Primary Examiner* — Mina Haghighatian
*Assistant Examiner* — Erin Hirt
(74) *Attorney, Agent, or Firm* — Stites & Harbison PLLC; Marvin Petry

(57) ABSTRACT

An inorganic silicate-substituted calcium phosphate hydroxyapatite, useful as a biomaterial, has a Ca/P molar ratio in the range 2.05 to 2.55 and a Ca/(P+Si) molar ratio less than 1.66. The hydroxyapatite can be substantially free of carbonate ions. The material has relatively high solubility and is able to release silicon into solution.

24 Claims, 9 Drawing Sheets

SILICATE-SUBSTITUTED HYDROXYAPATITE

TECHNICAL FIELD

The present invention relates to inorganic silicate-substituted hydroxyapatites, in particular silicate-substituted calcium phosphate hydroxyapatites intended for use as medical implant materials, their manufacture and use. The present invention also relates to biomaterials comprising hydroxyapatites of the present invention, and their use.

BACKGROUND OF THE INVENTION

Due to disease or trauma, surgeons need to replace bone tissue, and they can use bone grafts (autografts or allografts) or synthetic materials to replace bone during surgery. Amongst the types of synthetic materials used to replace bone, surgeons use metals (e.g. stainless steel hip or knee implants), polymers (e.g. polyethylene in acetabular cups), ceramics (e.g. hydroxyapatite as a macroporous bone graft) or inorganic-organic composites (e.g. hydroxyapatite-poly (lactic acid) composites for fixation plates). Many of these materials are not resorbable in the body (within a period appropriate to the healing period) and do not stimulate the formation of new bone around or within the implant.

One of the synthetic materials that has been developed over the past 30-40 years and can be used to replace bone is hydroxyapatite (HA, $Ca_{10}(PO_4)_6(OH)_2$). This material supports the growth of bone cells on its surface, and the formation of new bone, but it is very insoluble in the body, so can remain in the body for more than 10 years. For medical applications, hydroxyapatite is typically used as a coating, where it is subjected to high temperatures (>1500° C.) during the coating process, or as a macroporous ceramic, which contains large pores (>100 μm) and are produced by sintering the macroporous structure at high temperatures (e.g. 1200° C.)

To enhance the properties of hydroxyapatite, materials have been developed that contain small amounts of silicon or silicate ions. Silicon has been shown to play an important role in bone formation and in bone metabolism. The synthesis of a silicon-substituted hydroxyapatite material is described in WO 98/08773 and corresponding U.S. Pat. No. 6,312,468. The material comprises 0.1 to 5 wt % of silicon. The molar ratio of calcium ions to phosphorus-containing ions is 1:0.5 to 1:0.7. The most preferred silicon range is 0.5 to 1.0 wt %. On sintering, these materials were shown to be single phase compositions. Although these materials have been shown to accelerate the rate of bone healing in animal studies and in human clinical studies, these silicon-substituted materials are still very insoluble. A study by Guth et al., *Key Eng. Mater.*, 2006, 309-311, pp. 117-120, showed that the amount of silicon released from these materials on soaking for up to 14 days only reached levels of 0.1-0.4 ppm. Micro-porous ceramic disks of SiHA samples (silicon-substituted hydroxyapatite) containing 0.8 wt % silicon, equivalent to 2.6 wt % silicate, were soaked in a solution of cell culture medium.

Hydroxyapatite ceramics are not readily soluble in the body and will not disappear over a reasonable time period (C.P.A.T. Klein et al, *J. Biomed. Mater. Res.*, 1983, 17, 769). Suggested times for ideal complete resorption are between 1 month and 3 years, during which they would be replaced by new bone. It has also been shown that the release of calcium ions from materials such as calcium sulphate or calcium carbonate, and silicate ions from Bioglass (a CaO—SiO2—Na2O—P2O5 glass), can accelerate bone repair and/or stimulate osteoblasts (I. D. Xynos et al, *Calc. Tiss. Int.*, 2000, 67, 321-329).

US 2005/0244449 describes the synthesis of a silicon substituted oxyapatite compound (Si—OAp) for use as a synthetic bone biomaterial either used alone or in biomaterial compositions. The silicon-substituted oxyapatite compound has the formula:

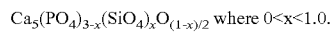

$Ca_5(PO_4)_{3-x}(SiO_4)_xO_{(1-x)/2}$ where $0<x<1.0$.

Synthesis of this material involves heating a synthetic calcium phosphate composition that contains silicon at high temperatures in a vacuum atmosphere, which removes all of the hydroxyl groups from the structure. The product has properties very different from those of silicon-substituted hydroxyapatite.

GB 395713 describes the synthesis of a silicon-containing apatite single crystal. The process produces single crystals having individual crystal long-axis lengths from 5 to 500 μm, and more typically 20 to 200 μm. The synthesis is performed at a temperature of between 70 and 150° C., and octacalcium phosphate is used as an intermediate phase. The product contains $CO_3$ and has a low silicon content in the range 0.4 to 2.4 wt % silicon, preferably 0.5-1% silicon. The Ca/P molar ratio is in the range 1:1.4 to 1:2, and the Ca/(P+Si) molar ratio is in the range 1:1.4 to 1:2.

EP1426066 describes the physical mixing, without reaction, of silica ($SiO_2$), calcia (CaO) and hydroxyapatite, with typically 67% by weight of the mixture existing as silicon (within the $SiO_2$). The three discrete oxide compounds are distributed in an organic polymer matrix. In GB 2363115, an implant material composed of porous and/or polycrystalline silicon is described. The silicon can be mixed into a calcium phosphate cement system or into a polymer, and exists as a discrete phase interspersed in a matrix of calcium phosphate.

JP-A-2002-137914 describes a hydroxyapatite containing silicate ions which is stated to have good ion exchange ability and antimicrobial activity. The powders obtained by the processes described, which were not calcined, have a ratio of Ca/(P+Si) at the stoichiometric level or higher. Carbonate ions are included in order to balance electric charge. It is believed that such powders will yield a hydroxyapatite containing a CaO phase on heating.

In Journal of Solid State Chemistry, 181 (2008) 1950-1960, Palard et al. describe the problem of achieving pure silicated hydroxyapatite without the presence of secondary phases. They prepared powders by an aqueous precipitation method, using a ratio of Ca/(P+Si) of 10/6. The powders contained carbonate. On calcination, carbonate-free apatites were obtained. Using the chemical formula

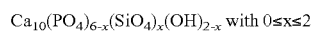

$Ca_{10}(PO_4)_{6-x}(SiO_4)_x(OH)_{2-x}$ with $0 \leq x \leq 2$ for the calcinated products, they report that the behaviour of the $Si_xHA$ powders with $x>1$ was very different from that of the compositions with $x \leq 1$. In the former case two phases simultaneously appeared from 700° C. The phases were identified as apatite and alpha tricalcium phosphate.

DISCLOSURE OF THE INVENTION

For clarification, the incorporation of silicon into an apatite or hydroxyapatite material can be referred to as silicon or silicate substitution. These terms can be used interchangeably. This is because the substitution is actually of a silicon atom substituting for a phosphorus atom in the apatite or hydroxyapatite lattice (strictly, the Si or P exists in the structure as an ion and not as a neutral atom). The phosphorus or silicon atom is, however, always associated with oxygen to form phosphates or silicates which in the invention may be, for example, but are not limited to, $SiO_4^{4-}$ or $PO_4^{3-}$ ions.

In one aspect, the present invention provides an inorganic silicate-substituted calcium phosphate hydroxyapatite, having a Ca/P molar ratio in the range 2.05 to 2.55 and a Ca/(P+Si) molar ratio less than 1.66. Preferably, the silicon atom content is in the range 2.9 to 6 wt %. In one embodiment, the hydroxyapatite of the present invention may be represented by formula (I):

$$Ca_{10-\delta}(PO_4)_{6-x}(SiO_4)_x(OH)_{2-x} \quad (I)$$

wherein $1.1 \leq x \leq 2.0$, and $\delta$ represents a Ca deficiency such that the Ca/(P+Si) molar ratio has a value less than 1.667 as herein described.

Preferably $1.2 \leq x \leq 2.0$, more preferably $1.4 \leq x \leq 2.0$ and most preferably $1.6 \leq x \leq 2.0$. Generally, it is desirable that the compound contains hydroxyl ions.

The silicate-substituted hydroxyapatites of the present invention have a high level of silicon incorporated into a hydroxyapatite phase that also contains calcium, phosphorus, oxygen and hydrogen ions, more specifically calcium, phosphate and hydroxyl ions. They have a hydroxyapatite structure, and preferably have sub-micron crystal morphology, in which case they are not classed as a ceramic or bioceramic which have monolithic structures and consist of fused grain structures that are separated by grain boundaries. The compound of the invention is preferably in the form of an unsintered material. This is achieved by heating the material at temperatures below the typical sintering temperature of hydroxyapatites during synthesis, so that sintering does not occur. Furthermore, the silicate-substituted hydroxyapatites of the present invention have a tendency to be thermally unstable at high temperatures; therefore they are preferably used as a powder or compacted powder, and are preferably not fused in the manner of sintered ceramic hydroxyapatites.

Advantageously, the hydroxyapatites of the present invention have been found to exhibit a high level of solubility compared to hydroxyapatite ceramics or previously reported silicon-substituted hydroxyapatite ceramics, and release high levels of silicon on soaking in solution. For example, approximately 10-100 times as much silicon is released from the silicate-substituted hydroxyapatites of the present invention compared to silicate-substituted hydroxyapatite ceramics described below, which are more similar to prior art materials, when tested under similar experimental conditions. It has also been observed that on soaking of the hydroxyapatite of the present invention in a physiological solution, such as cell culture medium, preferably for up to 48 hours, the calcium ion concentration of the culture medium is surprisingly unchanged, or increases. This contrasts with hydroxyapatites having lower levels of silicon substitution, which decrease the calcium content of the culture medium in the same time scale. Accordingly, the present invention can provide a new hydroxyapatite that is more active than known hydroxyapatites. It is able to release bone-stimulating ions readily and in high amounts to stimulate the formation of new bone, and at the same time is resorbable in the body within a healing period.

The silicon atom content of the silicate-substituted hydroxyapatites of the present invention is preferably at least 2.9 wt %, more preferably at least 3.5 wt %, and most preferably at least 5 wt %. These values are equivalent to a silicate ($SiO_4$) content of at least 9.5 wt %, at least 11.5 wt %, and at least 16 wt % respectively. A higher silicon content is desirable to release a larger amount of silicon when the hydroxyapatite is immersed in solution, in particular for biomedical applications used in bone formation and bone metabolism. Also, the properties of the hydroxyapatite are believed to change at a silicon atom content in the region of 2.9 wt % (9.5 wt % silicate) or above. The maximum silicon atom content is preferably 6 wt % (20 wt % silicate). The silicon atom content is preferably in the range 3.5 to 6 wt % (11.5 to 20 wt % silicate), and more preferably in the range 5 to 6 wt % (16 to 20 wt % silicate).

The molar ratio of calcium to phosphorus-containing ions (Ca/P molar ratio) is higher than that observed in stoichiometric hydroxyapatite (which is 10:6, or 1:0.6, or a Ca/P molar ratio of 1.67) or in prior art materials incorporating silicate in calcium phosphates discussed above. Accordingly, in one embodiment, the Ca/P molar ratio is at least 2.05

The molar ratio of Ca/(P+Si) is less than 1.66, preferably not more than 1.65, which is significantly lower than the Ca/(P+Si) molar ratio of 1.667 of other silicate-containing hydroxyapatite compositions. Preferably the Ca/(P+Si) molar ratio is in the range 1.50 to 1.65, more preferably in the range 1.60 to 1.65, yet more preferably in the range 1.60 to 1.64.

Preferably, the Ca/P molar ratio is at least 2.1, more preferably at least 2.2, and most preferably at least 2.3.

It is by designing the Ca/P molar ratio and the Ca/(P+Si) molar ratio to be within the ranges given here that 'space' within the structure is provided to enable the incorporation of high levels of silicon or silicate ions. Molar ratios of calcium to phosphorus-containing ions (written as Ca/P molar ratios) that are less than 2.05 (for example, Ca/P molar ratios of 2.0, 1.7 or 1.4) would result in insufficient 'space' in the structure for large quantities of silicon or silicate ions to exist. The only place in the structure that silicon can substitute is for phosphorus (it can not substitute for calcium or hydroxyl ions, or directly for oxygen ions).

The maximum Ca/P molar ratio is 2.55, preferably 2.5. Higher ratios than 2.55 are possible, but these will result in additional phases being present. Accordingly, the Ca/P molar ratio may be in the range 2.05 to 2.55, preferably 2.1 to 2.55, more preferably 2.2 to 2.5, or most preferably 2.3 to 2.5.

Preferably the hydroxyapatite material of the invention is free of carbonate ions ($CO_3$). The maximum impurity level of carbonate ions is preferably 0.1%, more preferably 0.01%, as a molar ratio based on the total of silicate and phosphoric ions. Thus carbonate substitution for phosphate (or silicate) in the composition is substantially absent.

Preferably, the hydroxyapatite is in crystalline form, particularly polycrystalline, e.g. polycrystalline particles. The crystallite average long-axis length may be 5 μm or less for improved solubility, and is preferably at least 0.05 μm. Preferably, the crystallite long-axis length is in the range 0.05 to 5 μm.

Preferably the specific surface area of the powder after heating is in the range 10 to 90 m$^2$/g, more preferably between 20 and 50 m$^2$/g. The specific surface area of the silicate-substituted hydroxyapatite powder produced by the present invention is significantly greater than the specific surface area of a hydroxyapatite powder (Ca/P=1.667, no Si) when the samples are heated at the same temperature. For example, after heating at 900° C. the specific surface area of one silicate-substituted hydroxyapatite powder produced by the present invention is 27 m$^2$/g, whereas the specific surface area of a corresponding unsubstituted hydroxyapatite powder is 13 m$^2$/g. The larger surface area of powders produced by the present invention may have beneficial effects on properties such as, but not limited to, solubility, protein adhesion and cell adhesion.

Preferably, the silicate-substituted hydroxyapatite particles of the present invention are substantially phase pure. This means that there are substantially no impurity phases. So, for example, only one polycrystalline phase may be seen by X-ray diffraction, with no secondary phases visible in the diffraction pattern. The presence of a single silicate-substituted hydroxyapatite phase can be determined using conventional X-ray diffraction analysis and comparing the obtained diffraction pattern with standard patterns for hydroxyapatite. The exact diffraction peak positions of the silicate-substituted hydroxyapatite phase show a small shift compared to the diffraction peak positions of a hydroxyapatite standard, as the substitution of silicate for phosphate results in a change in the unit cell parameter. This has previously been reported for small amounts of silicate substitution (e.g. I. R. Gibson et al, J. Biomed. Mater. Res. 44 (1999)422-428). The amount of silicon or silicate incorporated into the silicate-substituted hydroxyapatite, and the Ca/P molar ratio of the silicate-substituted hydroxyapatite may also be evaluated using chemical analysis techniques, for example, X-Ray Fluorescence (XRF). The silicate-substituted hydroxyapatite particles of the present invention are characterised by having a molar ratio as determined by XRF of Ca/(P+Si) less than 1.66, preferably not more than 1.65, e g not more than 1.64, and a Ca/P molar ratio of between 2.05 and 2.55. The composition should have a Ca/(P+Si) molar ratio less than 1.667 to ensure a single phase is obtained on heating. Using a design Ca/(P+Si) molar ratio of 1.667 and a design Ca/P molar ratio of 2.475 may result in a composition after heating at e.g. 900° C. containing a Si-containing HA phase and CaO as an impurity phase. In contrast a design Ca/(P+Si) molar ratio of 1.65 and a design Ca/P molar ratio of 2.475 results in a single Si-containing HA phase after heating at 900° C. with no CaO or other impurity phase present. FTIR analysis of the heat-treated silicate-substituted hydroxyapatite phase shows the presence of an OH stretching vibration between 3565 and 3580 cm$^{-1}$, indicating that hydroxyl groups still exist to some extent in the structure, confirming that the material is still a hydroxyapatite-like phase.

Whilst the hydroxyapatite polycrystalline particles of the present invention are preferably substantially free of impurity phases, they can be mixed as particles with one or more other components to enable introduction of additional properties to the material containing the silicate-substituted hydroxyapatite. Preferably in such a mixture the hydroxyapatite particles of the invention, which are typically phase pure, are embedded in a matrix of the other component or components. For example, when the hydroxyapatite is used in biomedical applications, a more complex biomedical material can be formed. In one embodiment, the silicate-substituted hydroxyapatite phase may be mixed with one or more other organic and/or inorganic materials, preferably at a ratio (by weight) of from 0.1:99.9 to 99.9:0.1, more preferably from 1:100 to 100:1.

The inorganic compounds which may be mixed with the compound of the invention include, but are not limited to, calcium carbonate, hydroxyapatite, substituted hydroxyapatite, tricalcium phosphate, calcium sulphate, calcium silicate, octacalcium phosphate, amorphous calcium phosphate, brushite, monetite, tetracalcium phosphate, calcium pyrophosphate, bioglass, calcium silicate glass, calcium silicate-based glass, calcium phosphate glass, calcium phosphate-based glass, calcium silicate-based glass-ceramic, calcium phosphate-based glass-ceramic, bioactive glasses, bioactive glass-ceramics, biocompatible glasses, biocompatible glass-ceramics, alumina and zirconia.

The organic compounds which may be mixed with the compound of the invention include, but are not limited to, polymers, natural polymers, synthetic polymers, biodegradable polymers, sugars, proteins, gels, lipids, drugs, growth factors, cytokines. The organic compound may optionally consist of one or more of, but not limited to, poly(lactic acid), polycaprolactone, poly(glycolic acid), poly(lactic-glycolic acid), other biodegradable polymers, mixtures of biodegradable polymers and copolymers of biodegradable polymers. Natural polymers may be employed, for example consisting of one or more of, but not limited to collagen, chitin, chitosan, cellulose and gelatine, or specific members of these families of polymers.

The silicate-substituted hydroxyapatites of the present invention can be used in biomaterials, such as biomedical materials, and can be used, for example, as medical implant materials, scaffolds for tissue engineering, or for supporting cell growth in tissue culture. These biomaterials are in the form of powder, granules or a bulk solid, or a combination of these. 'Powder' describes particles having an average particle size in the range 0.05 to 100 μm, and 'granules' describes particles having an average particle size in the range 100 μm to 10 mm. The porosity structure of these biomaterials may be mesoporous, microporous, macroporous, or a combination of these. The biomaterials may also be in the form of a coating that can be applied to a substrate using various techniques. Preferably, the biomaterial produced by the present invention contains a silicate-substituted hydroxyapatite phase of the present invention with no other phases present as observed by X-ray diffraction, but other phases may be intentionally added to form a mixture of the hydroxyapatite of the present invention and one or more of the inorganic and/or organic compounds described above.

In another aspect, the present invention relates to a biomedical device comprising a silicate-substituted hydroxyapatite according to the present invention. The biomedical device may comprise the silicate-substituted hydroxyapatite alone, or may optionally also contain one or more inorganic and/or organic phases. The biomedical device may be mixed with one or more biological entities which may be selected from, but are not limited to, cells, proteins, mRNA, and DNA.

In a further aspect, the present invention relates to the use of a silicate-substituted hydroxyapatite according to the present invention in a medical device, for example a medical implant. Examples of such a medical device are a scaffold material, a bone replacement material, a bone implant, a dental implant, a bone substitute, a dental substitute, a soft tissue substitute, a drug delivery device, a cell delivery device, a cell growth substrate, a medicinal product, a component of an organic-inorganic composite implant, a component of an organic-inorganic composite scaffold, a component of an organic-inorganic composite bone substitute, a component of an organic-inorganic spinal cage implant, a component of an organic-inorganic composite fixation screw implant, a component of an organic-inorganic composite fixation plate implant, a component of an organic-inorganic composite fixation implant, a component of an organic-inorganic composite fixation device, a coating, a cement, a component of a cement, a filler, and a filler supplement to another biomedical material.

In a further aspect, the ability of the silicate-substituted hydroxyapatites of the present invention to cause a sudden increase in pH when added to an aqueous solution can be used to form a composite with a polymer component such as, but not limited to, a solution of collagen. When the collagen solution is combined with the silicate-substituted hydroxyapatites of the present invention, the pH increase caused by the silicate-substituted hydroxyapatite results in gelation of the collagen solution.

The silicate-substituted hydroxyapatite according to the present invention may alternatively be used in other areas including, but not limited to, materials for use in chromatography, materials for use in purification methods such as the removal of heavy metals by adsorption, and catalyst materials.

Another aspect of the present invention is a process for manufacturing an inorganic silicate-substituted calcium phosphate hydroxyapatite, comprising:

(a) precipitation of silicate-substituted apatite from reactants containing calcium, phosphorus and silicon at a pH of at least 9, wherein the molar ratio of Ca/P of the reactants is in the range 2.05 to 2.55, and the Ca/(P+Si) molar ratio is less than 1.66, and (b) calcining the precipitate at a temperature in the range 400 to 1050° C.

In general, the words "apatite" and "hydroxyapatite" can be used interchangeably. "Hydroxyapatite" often refers to $Ca_{10}(PO_4)_6(OH)_2$, and an "apatite" is either a generic name for a material with the composition $M_{10}(XO_4)_6(L)_2$ (often a geological mineral), or in the case of calcium phosphates is used to describe an intermediate or non-stoichiometric form of hydroxyapatite. For clarity, as used herein, the term "silicate-substituted apatite" describes the material that is produced during the synthesis stage, before heating. On heating, a composition with a more defined composition is formed and is therefore described herein as a "silicate-substituted hydroxyapatite". This latter nomenclature is used to clarify that the material contains both silicate and hydroxyl ions.

The Ca/P molar ratio of the reactants of between 2.05 and 2.55 and a Ca/(P+Si) molar ratio of less than 1.66, preferably not more than 1.65, in the synthesis reaction allows large levels of silicate ions to be added (2.9 wt % to 6 wt % silicon, or 9.5 to 20 wt % silicate), and produces a silicate-substituted apatite that can be heated to produce an essentially phase pure silicate-substituted hydroxyapatite that does not contain significant amounts of additional phases.

The reactants are preferably essentially free of cations other than calcium and hydrogen ions, and preferably essentially free of anions other than phosphate, silicate and hydroxyl ions. The precipitation reaction is preferably carried out in aqueous conditions.

The synthesis may involve initially making an aqueous solution or suspension of calcium ions. This may be made using a calcium-containing reactant, such as a calcium salt or oxide. This may be, for example, calcium hydroxide, calcium oxide, calcium carbonate, calcium chloride or calcium nitrate. Alternatively, a mixture of calcium-containing reactants may be used.

A second solution of phosphorus ions may be made, for example, using a phosphorus-containing reactant such as a phosphate salt or phosphate acid. This may be, for example, phosphoric acid, ammonium phosphate, ammonium hydrogen phosphate or sodium phosphate. Alternatively, a mixture of phosphorus-containing reactants may be used.

The reactants are used in an amount such that the molar ratio of Ca/P is between 2.05 and 2.55. The greater this ratio, the less the amount of phosphorus-containing compound is used, and the greater the amount of silicon or silicate ions that may be substituted. In one embodiment, the Ca/P molar ratio of the reactants is at least 2.05, and the molar ratio of Ca/(P+Si) is in the range 1.50 to 1.65, preferably 1.60 to 1.65, more preferably 1.60 to 1.64. Preferably, the Ca/P molar ratio is at least 2.1, more preferably at least 2.2, and most preferably at least 2.3. The maximum Ca/P molar ratio is 2.55, preferably 2.5. Higher ratios than 2.55 are possible, but these may result in additional phases being present. Accordingly, the Ca/P molar ratio may be in the range 2.05 to 2.55, preferably 2.1 to 2.55, more preferably 2.2 to 2.5, or most preferably 2.3 to 2.5.

The silicon atom content of the reactants in the process of the present invention is preferably at least 2.9 wt %, more preferably at least 3.5 wt %, and most preferably at least 5 wt %. The maximum silicon atom content is preferably 6 wt %. The silicon atom content is preferably in the range 3.5 to 6 wt %, and more preferably in the range 5 to 6 wt %.

The precipitation reaction can be performed using more concentrated or less concentrated solutions. Higher concentration enables larger quantities of product to be obtained using smaller volumes of reactant solution, which has clear benefits for a large-scale process.

During the precipitation reaction, the phosphorus-containing solution (B) is preferably added to the calcium-containing solution/suspension (A). Alternatively, the calcium-containing solution/suspension (A) can be added to the phosphorus-containing solution (B). Alternatively, reactants (A) and (B) can be added at the same time to a reaction vessel. Preferably, when the phosphorus-containing solution (B) is added to the calcium-containing solution/suspension (A), it is added in a dispersed form, such as drop-wise, in a spray, or in small aliquots. The calcium-containing solution/suspension is stirred during the addition of the other reactant or reactants using, for example, a magnetic stirrer. This ensures that the local pH of the reaction mixture never drops too low, and always remains alkaline overall. The reaction may be carried out under conditions in which the reactants remain as solutions or suspensions, preferably at a temperature in the range 3 to 95° C., more preferably 10 to 50° C., and most preferably 15 to 25° C. or at room temperature.

The silicon in the precipitation reaction may be provided by a silicon-containing reactant, for example, an organosilicon compound, silicate salt or silicate acid, including but not limited to tetraethyl orthosilicate, tetramethyl orthosilicate, silicon acetate and silicic acid. Alternatively, a mixture of silicon-containing reactants can be used. The desired amount of silicon-containing reactant may be introduced in to the reaction mixture in a number of ways. The silicon-containing reactant may be used directly, or can be added to water, preferably deionised or distilled water, or added to an organic solvent, for example ethanol or acetone, or added to an alkali solution or an acidic solution. Preferably, the silicon-containing reactant is used directly. For illustrative purposes, if 0.099 moles of calcium hydroxide and 0.0417 moles of phosphoric acid are used (with a Ca/P molar ratio of 2.37), then 0.0183 moles of tetraethyl orthosilicate can be used. This achieves a design Ca/(P+Si) molar ratio of 1.65.

The silicon-containing reactant, or a solution containing the silicon-containing reactant, may be added to the reaction in various ways. Preferably, it is added to the calcium-containing solution/suspension (reactant A) prior to the addition of the phosphorus-containing solution (reactant B). Alternatively it may be added to the phosphorus-containing solution (reactant B), which is then added to the calcium-containing solution/suspension (reactant A). Another alternative is to add the silicon-containing compound, or a solution containing the silicon-containing compound, to the reaction mixture after the phosphorus-containing solution (reactant B) has been added to the calcium-containing solution/suspension (reactant A). Also, the silicon-containing compound, or a solution containing the silicon-containing compound, may be added simultaneously, with the phosphorus-containing solution (reactant B), to the calcium-containing solution/suspension (reactant A).

During the precipitation reaction, the pH is preferably maintained at 9 or above, more preferably 10 or above. The maximum pH may be 13, preferably 12. The pH may be maintained in the range 9 to 13, preferably in the range 10 to 12. The use of a Ca/P molar ratio in the range of 2.05 to 2.55 in the process means that, under certain experimental conditions, the pH of the reaction mixture is 'self-buffered' at a high pH, without the addition of an alkali/base, such as ammonia. This has significant benefits both environmentally and industrially as the synthesis does not require removal of harmful ammonia vapours. To result in a 'self-buffered' reaction mixture, the reactants should be chosen such that their behaviour in solution results in basic conditions. For example, if the calcium containing reactant is calcium hydroxide (Ca)(OH)$_2$), calcium oxide, or another calcium-containing compound that produces an alkaline pH in solution, when used at a Ca/P molar ratio of between 2.05 and 2.55, it will act under most conditions as a 'self-buffering' reactant. This may produce a solution with a very high pH (more than 10). As the Ca/P molar ratio is in the range of 2.05 to 2.55, even if the source of phosphorus-containing ions is an acid such as orthophosphoric acid, $H_3PO_4$, there will be relatively excess alkaline calcium hydroxide or calcium oxide relative to acidic phosphoric acid in the reaction mixture, so that even at the end of the reaction there will be more alkali than acid (i.e. this will not be a neutralisation reaction such as is observed in the synthesis of hydroxyapatite with a Ca/P molar ratio of 1.667). If the reaction does require adjustment to maintain the pH in the range 9 to 13, preferably in the range 10 to 12, then a suitable alkali/base is added, for example, ammonium hydroxide solution. In all specific examples of synthesis using the Ca/P ratios described here, no addition of an alkali/base is required, meaning that the synthesis is always self-buffered to a suitable high pH. This aspect of the embodiments of the present invention has important advantages of ease of large-scale manufacture (synthesis may be done in an open facility without air extraction to remove ammonia vapours) and also of environmental control, as the waste product of the reaction does not contain ammonia.

Upon complete addition of the reactants, the mixture may be stirred for a period of time to ensure thorough mixing. Typically, this is a period of 1 to 1000 minutes, preferably 30 to 360 minutes. After mixing, the precipitated reaction mixture is aged for a period of time to ensure complete reaction. This can be done at room temperature, or at lower (above freezing) or higher temperatures (up to and including at boiling point), and for a period of less than an hour to many weeks, but preferably for between 10 hours and 7 days, or more preferably between 16 hours and 3 days. After ageing, the reaction mixture is processed to separate the filtrate (solution) from the precipitated product. This can be done using, for example, an appropriate separation technique including, but not limited to, one of filtration, spray-drying and centrifugation. The collected solid may then be dried at room temperature or at elevated temperatures, or in a desiccator to form a dried product at the desired level of dryness. At this stage, the dried product, if dried as a solid product rather than spray dried to a powder or granules, may be either ground to a powder using a mill or other process of particle size reduction, or to granules by breaking up the solid product using a mill or other process of particle size reduction, followed by sieving if required. Alternatively, it may be retained as a solid bulk dried product.

The dried silicate-substituted hydroxyapatite phase is calcined or heated, preferably in an air atmosphere, at a temperature below the typical sintering temperature of hydroxyapatite bioceramics to increase crystallite/particle size, without resulting in traditional ceramic densification. The calcining or heating temperature is 1050° C. or less, preferably 1000° C. or less, and more preferably 900° C. or less. The minimum temperature is 400° C., preferably 600° C., or more preferably 700° C. This temperature may be in the range 400 to 1050° C., preferably in the range 600 to 1000° C., more preferably in the range 700 to 900° C., particularly about 700° C., for example 750 to 1000° C. It is desirable that the temperature is below the sintering temperatures of hydroxyapatite bioceramics, as sintering the material using temperatures greater than 1050° C. is likely to result in a rapid increase in the size of the crystallites, a large reduction in surface area, and also phase decomposition of the silicate-substituted hydroxyapatite to a multi-phase composition. For compositions containing 4.5 to 6 wt % Si substitution, e g 5 to 6 wt % Si substitution, with Ca/P ratios between 2.2 and 2.55, the preferred maximum heating temperature is 950° C., with the preferred heating temperature being in the range 600 and 950° C., and more preferably in the range 700 to 900° C., particularly about 700° C., for example 750 to 1000° C. The calcining or heating step may last for at least 1 second, preferably at least 1 minute, or more preferably at least 10 minutes. The maximum time for the calcining or heating step may be 200 hours, but is preferably 600 minutes, and more preferably 180 minutes. The time period for the calcining or heating step may be in the range 1 second to 200 hours, preferably in the range 1 to 600 minutes, more preferably in the range 10 to 180 minutes, with the time period selected based on the level of crystal size and/or surface area desired. The silicate-substituted hydroxyapatite phase can be calcined as a dried solid product, or as a powder or granule. Alternatively, the silicate-substituted hydroxyapatite can be calcined or heated without being dried after separation of the precipitated silicate-substituted hydroxyapatite compound from the filtrate.

In step (b), the silicate-substituted hydroxyapatite phase may be calcined or heated in an atmosphere containing water vapour. This may be achieved by supplying the furnace with air that has been passed through a container containing water or water vapour. The compound is supplemented with hydroxyl groups, or the existing hydroxyl groups are encouraged to remain with the compound during calcining/heating.

Alternative processes for manufacturing the silicate-substituted hydroxyapatites of the present invention can be used, for example, but not limited to, a sol-gel method or a hydrothermal method.

EMBODIMENTS OF THE INVENTION AND EXPERIMENTAL DATA

The present invention is now illustrated with reference to the following non-limiting examples and accompanying figures:

As used herein below, Control 1 is a hydroxyapatite having a Ca/P molar ratio of 1.67, no silicon, which has been heated at 1000° C. for 1 hour. Control 2 is a silicate-substituted hydroxyapatite having a Ca/P molar ratio of 1.75, 0.8 wt % silicon, which has been heated at 1000° C. for 1 hour.

EXAMPLE 1

Synthesis of a Silicate-Substitute Hydroxyapatite with a Ca/P Molar Ratio of 2.475, a Ca/(P+Si) Molar Ratio of 1.65 and a Silicon Content of Approximately 5.8 wt % (19 wt % Silicate).

0.495 moles of calcium hydroxide (36.679 g) were added to 1000 ml of deionised water and the aqueous suspension was stirred using a magnetic stirrer for about 10-15 minutes. 0.1 moles of tetraethyl orthosilicate (TEOS) (20.836 g) were added directly to the stirring calcium hydroxide suspension. This mixture was stirred for 5-10 minutes. 0.2 moles of orthophosphoric acid (23.053 g of 85% assay $H_3PO_4$) were added to 1000 ml of deionised water and stirred using a magnetic stirrer for about 5-10 minutes. The phosphoric acid solution was then placed in a dropping funnel and added drop-wise to the calcium hydroxide/TEOS suspension, over a period of about 60-120 minutes. After addition of the phosphoric acid solution, the pH of the reactant mixture was checked and the pH remained greater than 10, due to the high Ca/P molar ratio of the reactants used. No ammonia was therefore added. The reaction mixture was stirred for a further 2 hours and then allowed to age for approximately 24 hours. The whole reaction took place at room temperature. The suspension was then filtered using a Buchner funnel, filter paper and a vacuum pump. Once the filtrate had been removed, a wet filter-cake was obtained, which was then placed in a drying oven at 90° C. for approximately 2 days. After this, the dried filter-cake was removed, ground to a fine powder using a mortar and pestle, and then placed in a chamber furnace and heated in an air atmosphere to 900° C. for a period of one hour; a heating rate of 2.5° C./min and a cooling rate of 10° C./min were used. A small sample of the heated powder was used for characterisation using X-ray diffraction (XRD).

Figure 1:
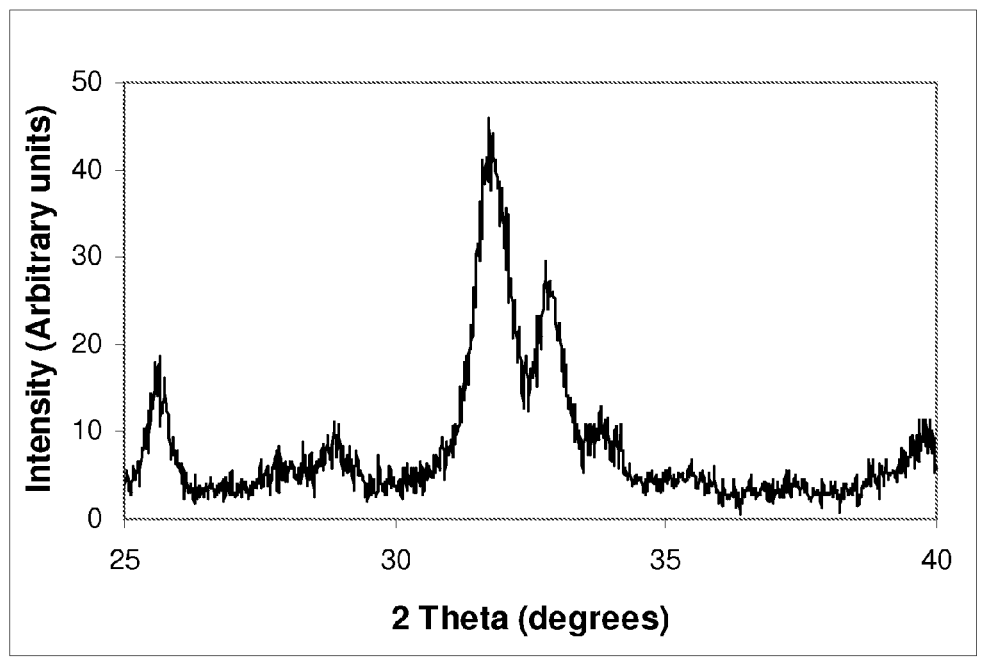
FIG. 1: X-ray diffraction (XRD) pattern for a silicate-substitute hydroxyapatite of the present invention having a Ca/P molar ratio of 2.475, a Ca/(P+Si) molar ratio of 1.65, and a silicon content of approximately 5.8 wt % (19 wt % silicate), after heating at 900° C. for 1 hour.

The XRD pattern of this sample is shown in FIG. 1. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite phase, compared to hydroxyapatite. The broad peaks are indicative of small crystals.

EXAMPLE 2

Synthesis of a Silicate-Substitute Hydroxyapatite with a Ca/P Molar Ratio of 2.36, a Ca/(P+Si) Molar Ratio of 1.65 and a Silicon Content of Approximately 5.2 wt % (17.1 wt % Silicate).

0.495 moles of calcium hydroxide (36.679 g) were added to 1000 ml of deionised water and the aqueous suspension was stirred using a magnetic stirrer for about 10-15 minutes. 0.09 moles of tetraethyl orthosilicate (TEOS) (18.750 g) were added directly to the stirring calcium hydroxide suspension. This mixture was stirred for 5-10 minutes. 0.21 moles of orthophosphoric acid (24.215 g of 85% assay $H_3PO_4$) were added to 1000 ml of deionised water and stirred using a magnetic stirrer for about 5 to 10 minutes. The phosphoric acid solution was then placed in a dropping funned and added drop-wise to the calcium hydroxide/TEOS suspension, over a period of about 60 to 120 minutes. After addition of the phosphoric acid solution, the pH of the reactant mixture was checked and the pH remained greater than 10, due to the high Ca/P molar ratio of the reactants used. No ammonia was therefore added. The reaction mixture was stirred for a further 2 hours and then allowed to age for approximately 24 hours. The whole reaction took place at room temperature. The suspension was then filtered using a Buchner funnel, filter paper and a vacuum pump. Once the filtrate had been removed, a wet filter-cake was obtained, which was then placed in a drying oven at 90° C. for approximately 2 days. After this, the dried filter-cake was removed, ground to a fine powder using a mortar and pestle, and then placed in a chamber furnace and heated in an air atmosphere to 900° C. for a period of one hour; a heating rate of 2.5° C./min and a cooling rate of 10° C./min were used. A small sample of the heated powder was used for characterisation using X-ray diffraction (XRD).

Figure 2:
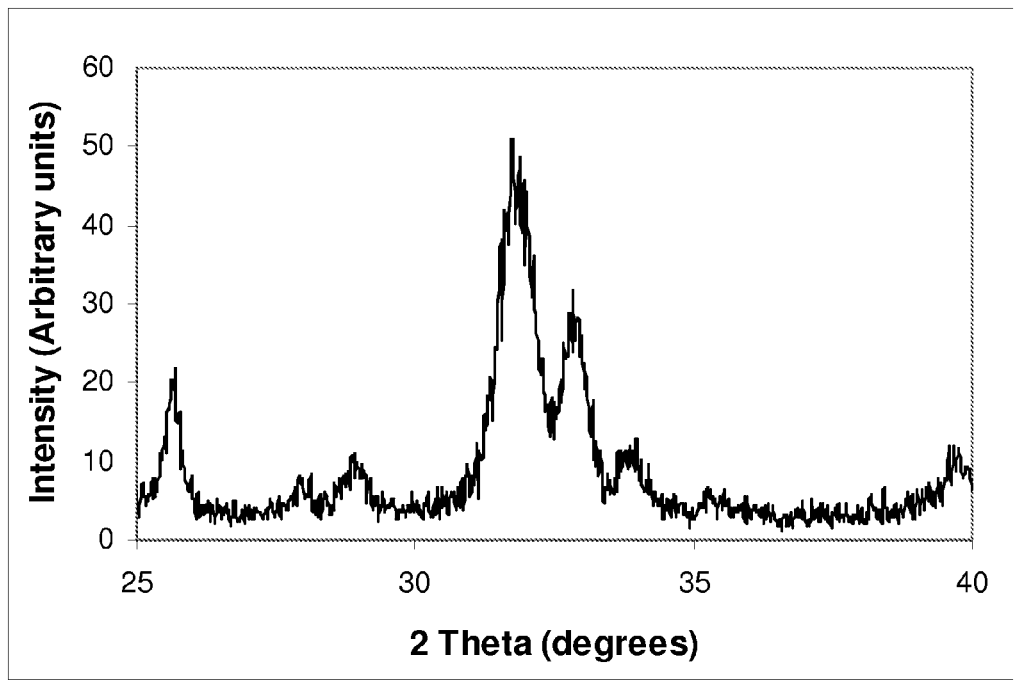
FIG. 2: X-ray diffraction (XRD) pattern for a silicate-substitute hydroxyapatite of the present invention having a Ca/P molar ratio of 2.36, a Ca/(P+Si) molar ratio of 1.65 and a silicon content of approximately 5.2 wt % (17.1 wt % silicate), after heating at 900° C. for 1 hour.

The XRD pattern of this sample is shown in FIG. 2. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite phase, compared to hydroxyapatite. The broad peaks are indicative of small crystals.

EXAMPLE 3

Synthesis of a Silicate-Substitute Hydroxyapatite with a Ca/P Molar Ratio of 2.25, a Ca/(P+Si) Molar Ratio of 1.65 and a Silicon Content of Approximately 4.6 wt % (15.1 wt % Silicate).

0.495 moles of calcium hydroxide (36.678 g) were added to 1000 ml of deionised water and the aqueous suspension was stirred using a magnetic stirrer for about 10-15 minutes. 0.08 moles of tetraethyl orthosilicate (TEOS) (16.664 g) were added directly to the stirring calcium hydroxide suspension. This mixture was stirred for 5-10 minutes. 0.22 moles of orthophosphoric acid was weighed out (25.362 g of 85% assay $H_3PO_4$) and this was added to 1000 ml of deionised water and stirred using a magnetic stirrer for about 5-10 minutes. The phosphoric acid solution was then placed in a dropping funnel and added drop-wise to the calcium hydroxide/TEOS suspension, over a period of about 60 to 120 minutes. After addition of the phosphoric acid solution, the pH of the reactant mixture was checked and the pH remained greater than 10, due to the high Ca/P molar ratio of the reactants used. No ammonia was therefore added. The reaction mixture was stirred for a further 2 hours and then allowed to age for approximately 24 hours. The whole reaction took place at room temperature. The suspension was then filtered using a Buchner funnel, filter paper and a vacuum pump. Once the filtrate had been removed, a wet filter-cake was obtained, which was then placed in a drying oven at 90° C. for approximately 2 days. After this, the dried filter-cake was removed, ground to a fine powder using a mortar and pestle, and then placed in a chamber furnace and heated in an air atmosphere to 900° C. for a period of one hour; a heating rate of 2.5° C./min and a cooling rate of 10° C./min were used. A small sample of the heated powder was used for characterisation using X-ray diffraction (XRD) and Fourier Transform Infrared (FTIR) spectroscopy.

Figure 3:
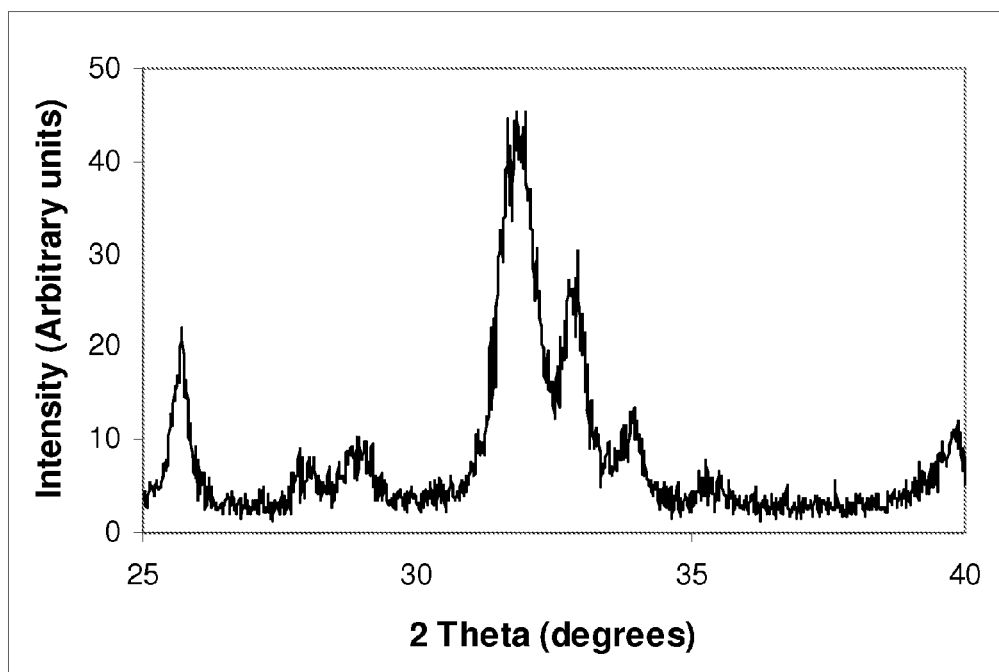
FIG. 3: X-ray diffraction (XRD) pattern for a silicate-substitute hydroxyapatite of the present invention having a Ca/P molar ratio of 2.25, a Ca/(P+Si) molar ratio of 1.65 and a silicon content of approximately 4.6 wt % (15.1 wt % silicate), after heating at 900° C. for 1 hour.

The XRD pattern of this sample is shown in FIG. 3. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite phase, compared to hydroxyapatite. The broad peaks are indicative of small crystals.

The unit cell parameters of this silicate-substituted hydroxyapatite phase, and of a stoichiometric hydroxyapatite with a Ca/P molar ratio of 1.67 and no silicon added, heated at 1000° C. for 1 hour (control 1), were determined using a Rietveld refinement software package and the results are listed in Table 1.

TABLE 1

| Sample | Ca/P molar ratio of sample | a-axis (Å) | c-axis (Å) |
|---|---|---|---|
| Example 3 | 2.25 | 9.442 | 6.939 |
| Control 1 | 1.67 | 9.427 | 6.885 |

Figure 4:
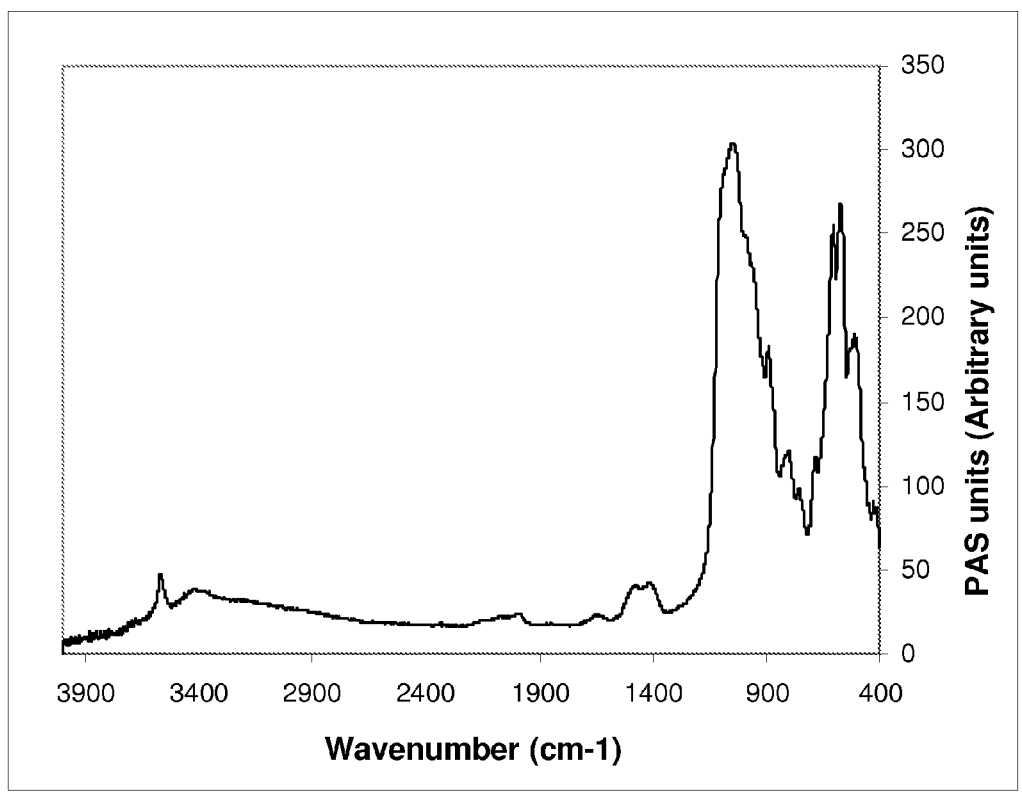
FIG. 4: FTIR spectrum of the silicate-substituted hydroxyapatite of FIG. 3.

The FTIR spectra of the silicate-substituted hydroxyapatite phase is shown in FIG. 4. The peak at approximately 3571 $cm^{-1}$ corresponds to a hydroxyl stretching vibration, indicating that the material does contain hydroxyl groups in the structure, so can be classed as a hydroxyapatite phase. The peaks at approximately 997, 893, 828, 810, 760, 687, 529, 510 $cm^{-1}$ correspond to vibrations that are the result of the silicate substitution.

EXAMPLE 4

Synthesis of a Silicate-Substitute Hydroxyapatite with a Designed Ca/P Molar Ratio of 2.15, a Ca/(P+Si) Molar Ratio of 1.65 and a Silicon Content of Approximately 4.0 wt % (13.2 wt % Silicate).

0.495 moles of calcium hydroxide (36.679 g) were added to 1000 ml of deionised water and the aqueous suspension was stirred using a magnetic stirrer for about 10-15 minutes. 0.07 moles of tetraethyl orthosilicate (TEOS) (14.583 g) were added directly to the stirring calcium hydroxide suspension. This mixture was stirred for 5-10 minutes. 0.23 moles of orthophosphoric acid were weighed out (26.516 g of 85% assay $H_3PO_4$) and this was added to 1000 ml of deionised water and stirred using a magnetic stirrer for about 5-10 minutes. The phosphoric acid solution was then placed in a dropping funnel and added drop-wise to the calcium hydroxide/TEOS suspension, over a period of about 45-60 minutes. After addition of the phosphoric acid solution, the pH of the reactant mixture was checked and the pH remained greater than 10, due to the high Ca/P molar ratio of the reactants used. No ammonia was therefore added. The reaction mixture was stirred for a further 2 hours and then allowed to age for approximately 24 hours. The whole reaction took place at room temperature. The suspension was then filtered using a Buchner funnel, filter paper and a vacuum pump. Once the filtrate had been removed, a wet filter-cake was obtained, which was then placed in a drying oven at 90° C. for approximately 2 days. After this, the dried filter-cake was removed, ground to a fine powder using a mortar and pestle, and then placed in a chamber furnace and heated in an air atmosphere to 900° C. for a period of one hour; a heating rate of 2.5° C./min and a cooling rate of 10° C./min were used. A small sample of the heated powder was used for characterisation using X-ray diffraction (XRD) and Fourier Transform Infrared (FTIR) spectroscopy.

Figure 5:
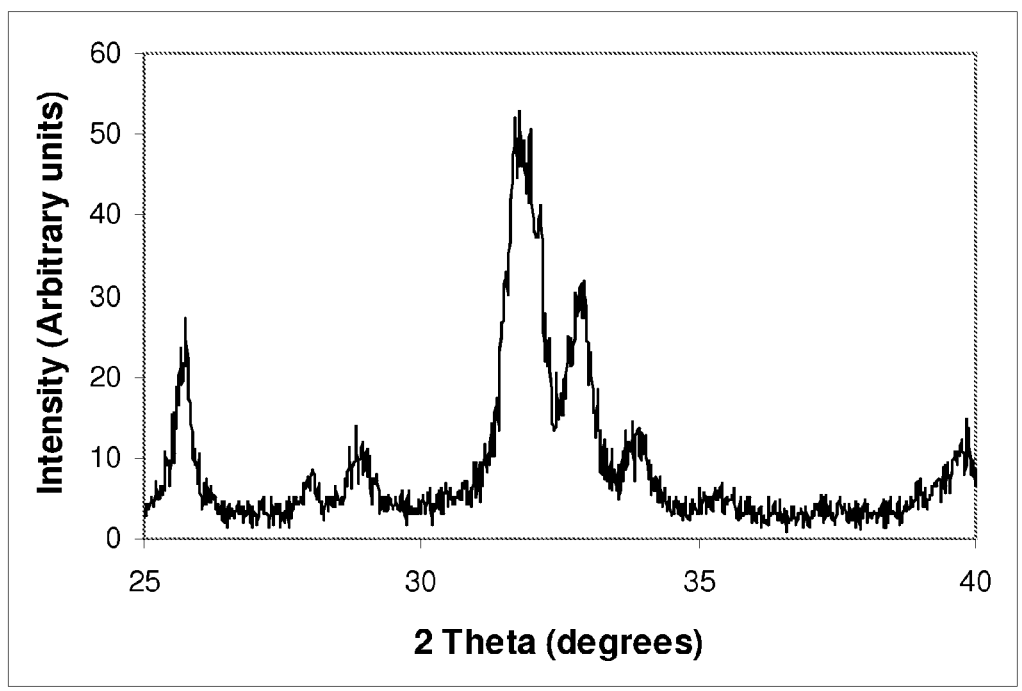
FIG. 5: X-ray diffraction (XRD) pattern for a silicate-substitute hydroxyapatite of the present invention having a Ca/P molar ratio of 2.15, a Ca/(P+Si) molar ratio of 1.65 and a silicon content of approximately 4.0 wt % (13.2 wt % silicate), after heating at 900° C. for 1 hour.

The XRD pattern of this sample is shown in FIG. 5. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite-like phase, compared to hydroxyapatite. The broad peaks are indicative of small crystals.

The unit cell parameters of this silicate-substituted hydroxyapatite-like phase, and of a hydroxyapatite with a Ca/P molar ratio of 1.67 and no silicon added, heated at 1000° C. for 1 hour (Control 1), were determined using a Rietveld refinement software package; the results are listed in Table 2.

TABLE 2

| Sample | Ca/P molar ratio of sample | a-axis (Å) | c-axis (Å) |
|---|---|---|---|
| Example 4 | 2.15 | 9.431 | 6.933 |
| Control 1 | 1.67 | 9.427 | 6.885 |

Figure 6:
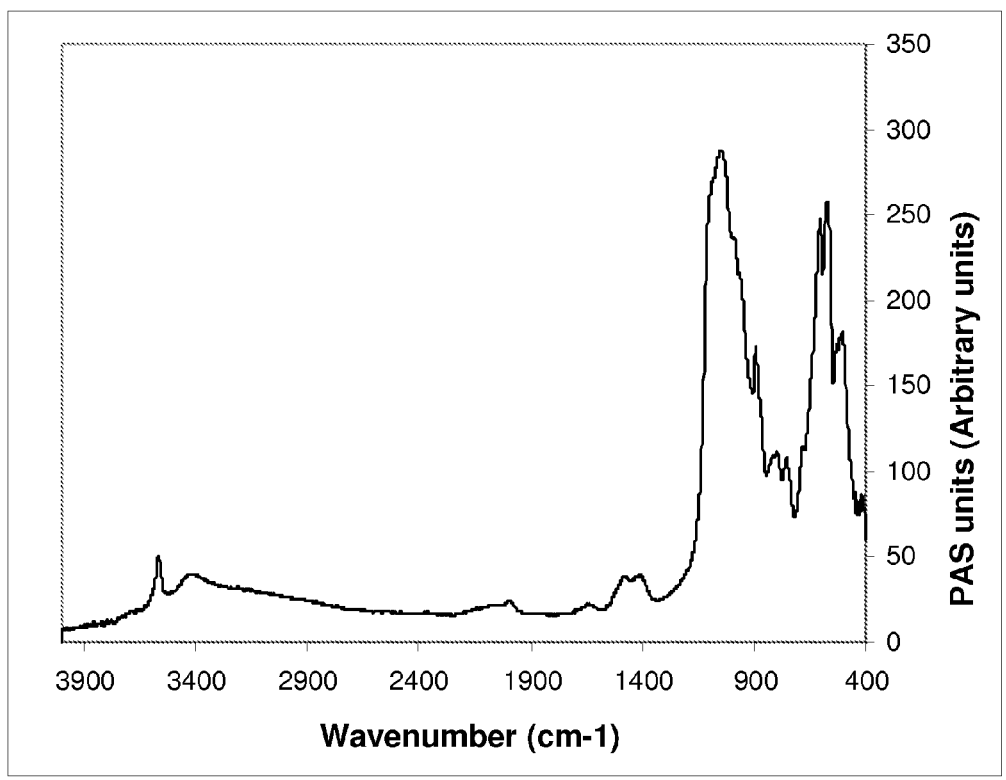
FIG. 6: FTIR spectrum of the silicate-substituted hydroxyapatite of FIG. 5.

An FTIR spectrum of the silicate-substituted hydroxyapatite-like phase is shown in FIG. 6; the peak at approximately 3570 $cm^{-1}$ corresponds to a hydroxyl stretching vibration, indicating that the material does contain hydroxyl groups in the structure, so can be classed as a hydroxyapatite-like phase. The peaks at approximately 997, 893, 828, 810, 760, 687, 529, 510 cm$^{-1}$ correspond to vibrations that are the result of the silicate substitution.

EXAMPLE 5

Measurement of the Relative Solubility of Silicate-Substitute Hydroxyapatites with a Ca/P Molar Ratio Between 2.05 and 2.55, and a Silicon Content of Between 3 and 6 wt % (9.5 and 20 wt % Silicate)

Powders of heat-treated samples from Examples 1 and 4 and control samples of hydroxyapatite (Ca/P molar ratio=1.67, no silicon, heated at 1000° C., Control 1) and a silicate-substituted hydroxyapatite (Ca/P molar ratio=1.75, 0.8 wt % silicon, heated at 1000° C., Control 2) were tested to determine how much silicon was released on soaking in a physiological solution. Each powder was milled in a ball mill to reduce the particle size. For each sample, a portion (0.5 g) was added to 50 mL of Dulbecco's Modified Eagle's Medium (DMEM, a standard cell culture medium) in a sterile plastic bottle. Bottles were placed on an orbital shaker at room temperature to constantly mix the powder in the soaking solution; this was done at room temperature. After an appropriate time point, solutions were removed and passed through a 0.2 μm filter. The filtered solutions were then analysed by ICP-OES (Inductively Coupled Plasma—Optical Emission Spectroscopy) to measure the silicon ion and calcium ion concentrations in the soaking solutions.

The results for the Si ion concentration (μg/ml, which is equivalent to ppm) of Example 1 and Controls 1 and 2 after soaking for 1 hour are listed in Table 3.

TABLE 3

| Sample | Ca/P molar ratio of sample | Si substitution (wt %) in sample | Si ion concentration released into DMEM after soaking for 1 hour (μg/ml) |
|---|---|---|---|
| Example 1 | 2.475 | 5.8 | 17 |
| Control 1 | 1.67 | 0 | <0.02 |
| Control 2 | 1.75 | 0.8 | 0.06 |

The results for the Ca ion concentration of the DMEM culture medium (μg/ml, which is equivalent to ppm) after soaking compositions of Example 1 and Controls 1 and 2 for 1 hour are listed in Table 4.

TABLE 4

| Sample | Ca/P molar ratio of sample | Si substitution (wt %) in sample | Ca ion concentration of DMEM after soaking for 1 hour (μg/ml) |
|---|---|---|---|
| Example 1 | 2.475 | 5.8 | 58 |
| Control 1 | 1.67 | 0 | 47 |
| Control 2 | 1.75 | 0.8 | 40 |

The results for the Si ion concentration (μg/ml, which is equivalent to ppm) of Example 4 and Controls 1 and 2 after soaking for 1 day are listed in Table 5.

TABLE 5

| Sample | Ca/P molar ratio of sample | Si substitution (wt %) in sample | Si ion concentration released into DMEM after soaking for 1 day (μg/ml) |
|---|---|---|---|
| Example 4 | 2.15 | 4.0 | 35 |
| Control 1 | 1.67 | 0 | <0.02 |
| Control 2 | 1.75 | 0.8 | 0.5 |

The results for the Ca ion concentration of the DMEM culture medium (μg/ml, which is equivalent to ppm) after soaking compositions of Example 4 and Controls 1 and 2 for 1 day are listed in Table 6.

TABLE 6

| Sample | Ca/P molar ratio of sample | Si substitution (wt %) in sample | Ca ion concentration of DMEM after soaking for 1 day (μg/ml) |
|---|---|---|---|
| Example 4 | 2.15 | 4.0 | 70 |
| Control 1 | 1.67 | 0 | 42 |
| Control 2 | 1.75 | 0.8 | 33 |

EXAMPLE 6

Synthesis of a Silicate-Substitute Hydroxyapatite with a Ca/P Molar Ratio of 2.475, a Ca/(P+Si) Molar Ratio of 1.65 and a Silicon Content of Approximately 5.8 wt % (19 wt % Silicate) Using Higher Concentrations of Reactants.

The precipitation reaction described in Examples 1-4 can be carried using more concentrated or less concentrated solutions. For example, for a Ca/P molar ratio of 2.475 made at a concentration 4 times that of Example 1, then 0.495 moles of calcium hydroxide (36.679 g) will be added to 250 ml of water, preferably deionised water or distilled water (reactant A) and 0.2 moles of phosphoric acid (23.053 g) will be added to 250 ml of water, preferably deionised water or distilled water (reactant B). For this example, the amount of tetraethyl orthosilicate to be used will be 0.1 moles (20.836 g) and this will be added to reactant A. This will enable larger quantities of product to be obtained using smaller volumes of reactant solution, which has clear benefits for a large-scale process. The precipitation process and the subsequent processing steps will be the same as those described in Examples 1-4. Using higher concentrations of reactants does require efficient stirring of the reaction mixture, but allows smaller volumes of reactant solution to be used to obtain comparable levels of product, but also may shorten the time required to add the phosphoric acid solution to the Ca(OH)$_2$/TEOS solution/suspension. This precipitation was repeated three times using exactly the same conditions, producing batches termed Synthesis 1, Synthesis 2 and Synthesis 3.

Figure 7:
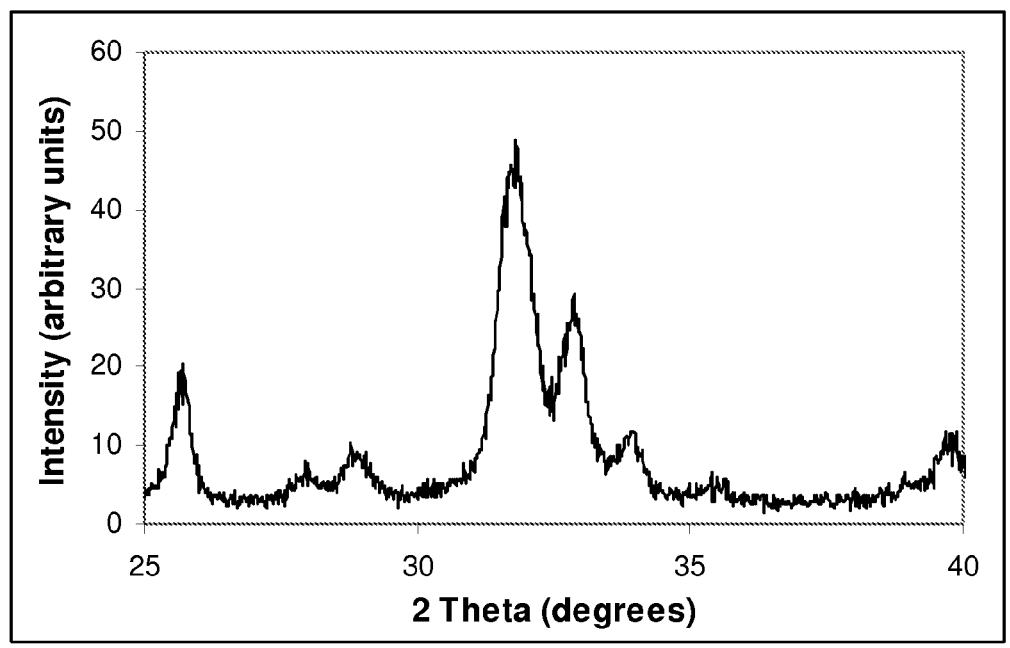
FIG. 7: X-ray diffraction (XRD) pattern for a silicate-substitute hydroxyapatite of the present invention having a Ca/P molar ratio of 2.36, a Ca/(P+Si) molar ratio of 1.65 and a silicon content of approximately 5.2 wt % (17.1 wt % silicate) using higher concentrations of reactants, after heating at 900° C. for 1 hour.

In this specific example, the product was heated at 900° C. for one hour. The XRD pattern of this sample (Synthesis 1) is shown in FIG. 7; data were collected over a longer time period that data presented in the other figures. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite-like phase, compared to hydroxyapatite. The broad peaks are indicative of small crystals and the peak positions are indicative of an apatite-like phase.

X-ray fluorescence measurements of the triplicate samples allowed the amounts of Ca, P and Si were determined and compared with the designed values, the results being given in Table 7. The amounts of silicon (or silicate) incorporated into the compositions are comparable and similar to the theoretical values. The molar ratios Ca/P and Ca/(P+Si) are all comparable between the three separate syntheses and are slightly lower than the design composition. It is clear from this data and from the XRD data that to produce a single phase material containing e.g. 5.8 wt % Si after heating at 900° C., a Ca/(P+Si) molar ratio of less than 1.667 (typical value for HA and other reported Si-HA materials with low levels of Si substitution) is required. For example, synthesis with a design composition of Ca/(P+Si) molar ratio of 1.65 achieves a single phase with no impurities, and this results in an actual Ca/(P+Si) molar ratio of the product of 1.63. An example of a synthesis with a design Ca/(P+Si) molar ratio of 1.667 and the impurity phase obtained is given in Example 8.

TABLE 7

| | XRF Experimental values | | |
| Theoretical Values | Synthesis 1 | Synthesis 2 | Synthesis 3 |
| --- | --- | --- | --- |
| Wt % Si 5.82 | 5.79 | 5.80 | 5.81 |
| Wt % SiO$_4$ 19.09 | 19.00 | 19.03 | 19.06 |
| Ca/P 2.475 | 2.43 | 2.43 | 2.43 |
| Ca/(P + Si) 1.65 | 1.63 | 1.63 | 1.63 |

EXAMPLE 7

Synthesis of a Silicate-Substitute Hydroxyapatite with a Designed Ca/P Molar Ratio of 2.36, a Ca/(P+Si) Molar Ratio of 1.65 and a Silicon Content of Approximately 5.2 wt % (17.1 wt % Silicate), Heated at Temperatures Between 600 and 900° C.

The process of Example 2 was repeated four separate times using the same Ca/P molar ratio and silicon content, each time at a different temperature of 600, 700, 800 and 900° C. respectively for the final heating step. A heating rate of 2.5° C./min and a cooling rate of 10° C./min were used. A small sample of each powder heated at the various temperatures was used for characterisation using X-ray diffraction (XRD).

Figure 8:
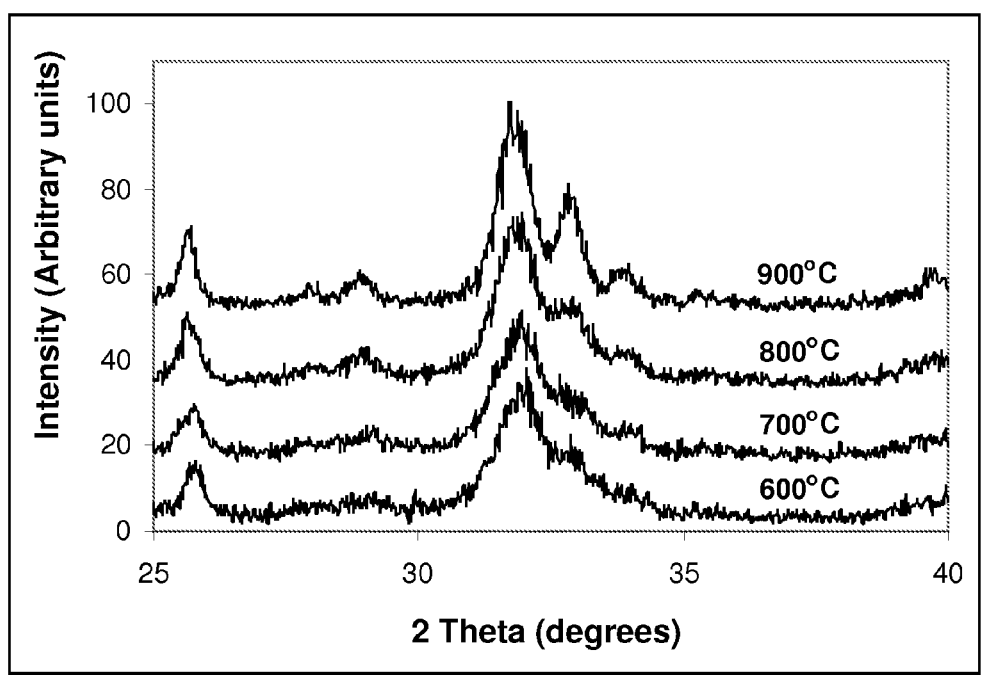
FIG. 8: X-ray diffraction (XRD) patterns for silicate-substitute hydroxyapatites of the present invention having a Ca/P molar ratio of 2.36, a Ca/(P+Si) molar ratio of 1.65 and a silicon content of approximately 5.2 wt % (17.1 wt % silicate), which have each been heated at a different temperature of 600, 700, 800 and 900° C. respectively.

The XRD pattern of this sample is shown in FIG. 8. It can be observed that all the diffraction peaks can be matched to peak positions of a standard pattern of hydroxyapatite, with no secondary phases present. The diffraction peak positions have shifted, suggesting a change in the unit cell parameters of the silicate-substituted hydroxyapatite-like phase, compared to hydroxyapatite. As the heating temperature is increased, the peaks become narrower, which is indicative of an increase in the crystallite size. By choosing a specific heating temperature, the crystal size of the materials can be controlled.

EXAMPLE 8

COMPARATIVE EXAMPLE

Synthesis of a Silicate-Substitute Hydroxyapatite with a Ca/P Molar Ratio of 2.38, a Ca/(P+Si) Molar Ratio of 1.667 and a Silicon Content of Approximately 5.2 wt % (17.1 wt % Silicate).

0.5 moles of calcium hydroxide (37.049 g) were added to 1000 ml of deionised water and the aqueous suspension was stirred using a magnetic stirrer for about 10-15 minutes. 0.09 moles of tetraethyl orthosilicate (TEOS) (18.750 g) were added directly to the stirring calcium hydroxide suspension. This mixture was stirred for 5-10 minutes. 0.21 moles of orthophosphoric acid (24.215 g of 85% assay H$_3$PO$_4$) were added to 1000 ml of deionised water and stirred using a magnetic stirrer for about 5-10 minutes. The phosphoric acid solution was then placed in a dropping funnel and added drop-wise to the calcium hydroxide/TEOS suspension, over a period of about 60-120 minutes. After addition of the phosphoric acid solution, the pH of the reactant mixture was checked and the pH remained greater than 10, due to the high Ca/P molar ratio of the reactants used. No ammonia was therefore added. The reaction mixture was stirred for a further 2 hours and then allowed to age for approximately 24 hours. The whole reaction took place at room temperature. The suspension was then filtered using a Buchner funnel, filter paper and a vacuum pump. Once the filtrate had been removed, a wet filter-cake was obtained, which was then placed in a drying oven at 90° C. for approximately 2 days. After this, the dried filter-cake was removed, ground to a fine powder using a mortar and pestle, and then placed in a chamber furnace and heated in an air atmosphere to 900° C. for a period of one hour; a heating rate of 2.5° C./min and a cooling rate of 10° C./min were used. A small sample of the heated powder was used for characterisation using X-ray diffraction (XRD).

Figure 9:
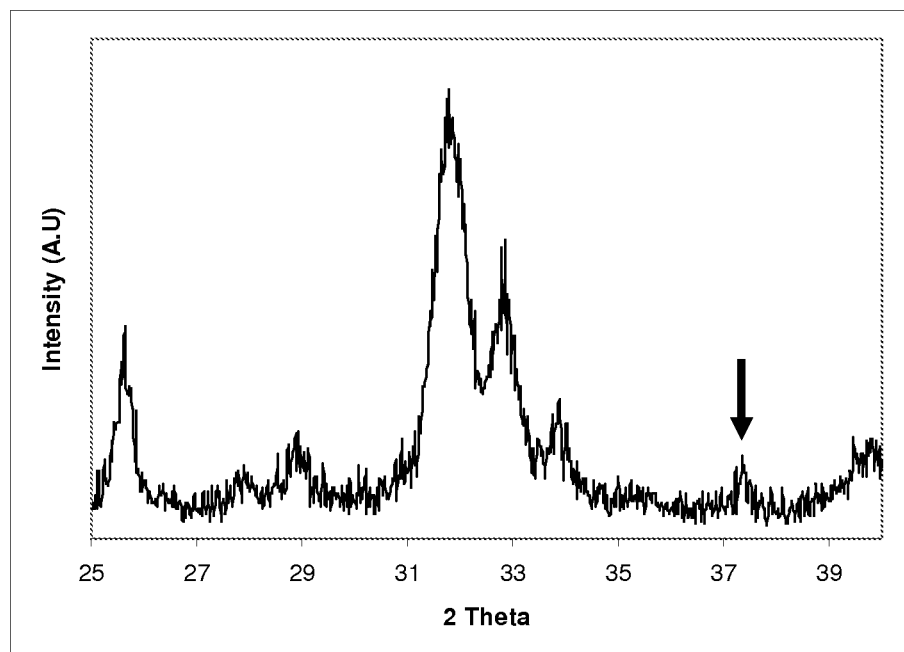
FIG. 9: X-ray diffraction (XRD) pattern for a comparative silicate-substitute hydroxyapatite having a Ca/P molar ratio of 2.38, a Ca/(P+Si) molar ratio of 1.667 and a silicon content of approximately 5.2 wt % (17.1 wt % silicate), after heating at 900° C. for 1 hour, showing the presence of an impurity phase of CaO (arrow).

The XRD pattern of this sample is shown in FIG. 9. It can be observed that the diffraction peaks can be matched to peak positions of either a standard pattern of hydroxyapatite, or to a second phase of calcium oxide (e.g the diffraction peak at approx. 37.5° 2 theta, marked with an arrow). If this result is compared with that obtained for EXAMPLE 2, FIG. 2, which is produced with a similar amount of Si added, but with a designed Ca/(P+Si) molar ratio of 1.65. This example demonstrates that if a design Ca/(P+Si) molar ratio of 1.667 is used then a single phase product is not obtained, unlike the case for a design ratio of 1.65 (EXAMPLE 2), but a mixture of an HA-like phase and CaO are obtained, FIG. 9. Similarly, if compositions similar to EXAMPLES 1, 3 and 4 are made but with a design Ca/(P+Si) molar ratio of 1.667, rather than 1.65, an impurity phase of CaO is also obtained upon heating at e.g. 900° C.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

What is claimed is:

1. A crystalline inorganic silicate-substituted calcium phosphate hydroxyapatite, having a Ca/P molar ratio in the range of 2.05 to 2.55 and a Ca/(P+Si) molar ratio in the range of 1.60 to 1.65.

2. A hydroxyapatite according to claim 1, wherein the silicon atom content is in the range of 2.9 to 6 wt %.

3. A hydroxyapatite according to claim 1, wherein the hydroxyapatite is free of impurity phases.

4. A hydroxyapatite according to claim 1, wherein the Ca/P molar ratio is in the range of 2.3 to 2.5.

5. A hydroxyapatite according to claim 1 wherein the Ca/(P+Si) molar ratio is in the range of 1.60 to 1.64.

6. A hydroxyapatite according to claim 1, wherein a maximum impurity level of carbonate ions is 0.1% as a molar ratio based on a total of silicate and phosphate ions.

7. A composition comprising a mixture of hydroxyapatite according to claim 1 and at least one other component.

8. A process for manufacturing an inorganic silicate-substituted calcium phosphate hydroxyapatite, comprising:
   (a) precipitation of silicate-substituted apatite from reactants containing calcium, phosphorus and silicon at a pH of at least 9, wherein the molar ratio of Ca/P of the reactants is in the range of 2.05 to 2.55 and the molar ratio Ca/(P +Si) is in the range of 1.60 to 1.65, and
   (b) calcining the precipitate at a temperature in the range of 400 to 1050° C.

9. A process according to claim 8, wherein the silicon atom content of the reactants is in the range of 2.9 to 6 wt %.

10. A process according to claim 8, comprising ageing the precipitate before calcining.

11. A process according to claim 8, wherein the reactants include a calcium-containing reactant selected from the group consisting of: calcium hydroxide, calcium oxide, calcium carbonate, calcium chloride and calcium nitrate.

12. A process according to claim 8, wherein the pH of the precipitation reaction is maintained in the range of 10 to 12.

13. A process according to claim 8, wherein the calcining temperature is in the range of 700 to 1000° C.

14. A process according to claim 8, wherein in step (b) the precipitate is calcined in an atmosphere containing water vapour.

15. A process according to claim 8, wherein the silicon-containing reactant is added to the calcium-containing reactant, before addition of the phosphorus-containing reactant.

16. A process according to claim 8, wherein the Ca/P molar ratio is in the range of 2.2 to 2.5.

17. A medical device containing a hydroxyapatite according to claim 1.

18. A medical device according to claim 17, which is selected from the group consisting of: a medical implant, a scaffold material, a bone replacement material, a bone implant, a dental implant, a bone substitute, a dental substitute, a soft tissue substitute, a drug delivery device, a cell delivery device, a cell growth substrate, a medicinal product, a component of an organic-inorganic composite implant, a component of an organic-inorganic composite scaffold, a component of an organic-inorganic composite bone substitute, a component of an organic-inorganic spinal cage implant, a component of an organic-inorganic composite fixation screw implant, a component of an organic-inorganic composite fixation plate implant, a component of an organic-inorganic composite fixation implant, a component of an organic-inorganic composite fixation device, a coating, a cement, a component of a cement, a filler or a filler supplement to another biomedical material.

19. A method for stimulating new bone formation, the method comprising implanting a medical implant material in a patient to release bone-stimulating ions to stimulate the formation of new bone, wherein the material is a crystalline inorganic silicate-substituted hydroxyapatite having a Ca/P molar ratio in the range of 2.05 to 2.55 and a Ca/(P+Si) molar ratio in the range of 1.60 to 1.65.

20. The method of claim 19, wherein the silicon atom content is in the range of 2.9 to 6 wt %.

21. The method of claim 19, wherein the hydroxyapatite is free of impurity phases.

22. The method of claim 19, wherein the Ca/P molar ratio is in the range of 2.3 to 2.5.

23. The method of claim 19, wherein the Ca/(P+Si) molar ratio is in the range of 1.60 to 1.64.

24. The method of claim 19, wherein a maximum impurity level of carbonate ions is 0.1% as a molar ratio based on a total of silicate and phosphate ions.

* * * * *